United States Patent [19]

Lucini

[11] Patent Number: 5,603,689
[45] Date of Patent: Feb. 18, 1997

[54] ELEVATOR DEVICE FOR AN ABDOMINAL WALL, IN VIDEOLAPAROSCOPIC SURGICAL OPERATIONS

[75] Inventor: Flavio Lucini, Ospiate Di Bollate, Italy

[73] Assignee: L & T S.n.c. di Ermanno Lucini & C., Milan, Italy

[21] Appl. No.: 426,864

[22] Filed: Apr. 24, 1995

[30] Foreign Application Priority Data

Aug. 5, 1994 [IT] Italy .................................. MI94A1705
Mar. 22, 1995 [IT] Italy .................................. MI950196 U

[51] Int. Cl.⁶ .............................. A61B 1/22; A61B 17/02
[52] U.S. Cl. ........................ 600/201; 600/204; 600/210; 600/217; 600/227
[58] Field of Search ..................... 600/201, 204, 600/206, 208–211, 217, 219, 227; 606/185, 191; 604/106, 222, 223

[56] References Cited

U.S. PATENT DOCUMENTS 1,441,298  1/1923  Pineiro .................... 600/217
2,977,958  4/1961  Seiger ..................... 600/227
3,467,079  9/1969  James ..................... 600/210
5,183,033  2/1993  Wilk ....................... 600/204
5,441,513  8/1995  Roth ....................... 606/185

FOREIGN PATENT DOCUMENTS

95/08952  4/1995  WIPO .................... A61B 17/02

Primary Examiner—Richard J. Apley
Assistant Examiner—Beverly M. Flanagan
Attorney, Agent, or Firm—Browdy and Neimark

[57] ABSTRACT

An elevator device for an abdominal wall in videolaparoscopic surgical operations is provided, which comprises mechanical elements (8) for tensioning an abdominal wall (10) and movement means (2) for the mechanical tensioning elements (8), in which the mechanical tensioning elements (8) are embodied by shaped needles having sharpened ends (14a) adapted to be introduced into the subcutaneous tissue (9) of the abdominal wall (10), and in which the movement means (2) comprises raising members (6) and spacing members (28) to move the shaped needles (8) away from each other, adapted to carry out raising of the abdominal wall (10) and tensioning of same transversally of said raising.

14 Claims, 5 Drawing Sheets

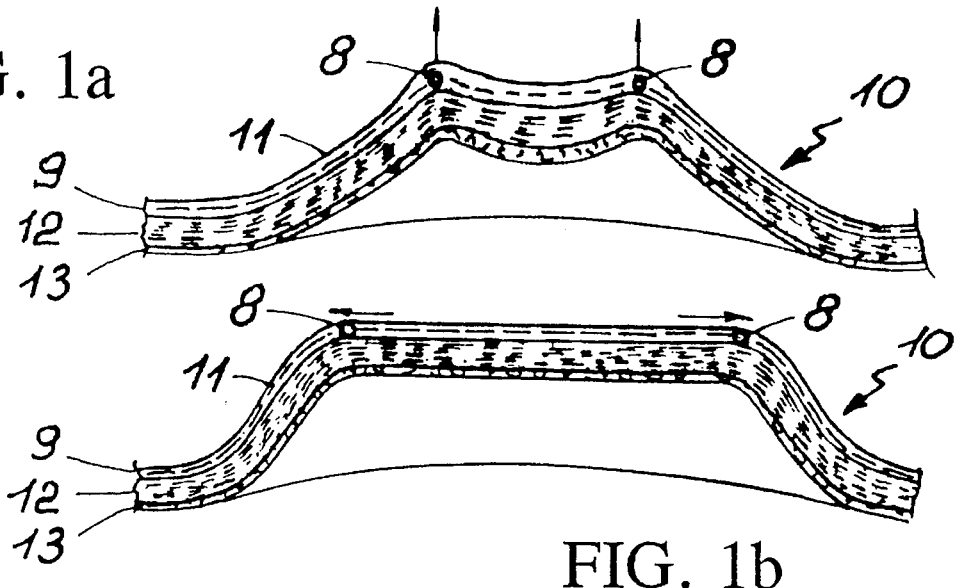
FIG. 1a
FIG. 1b
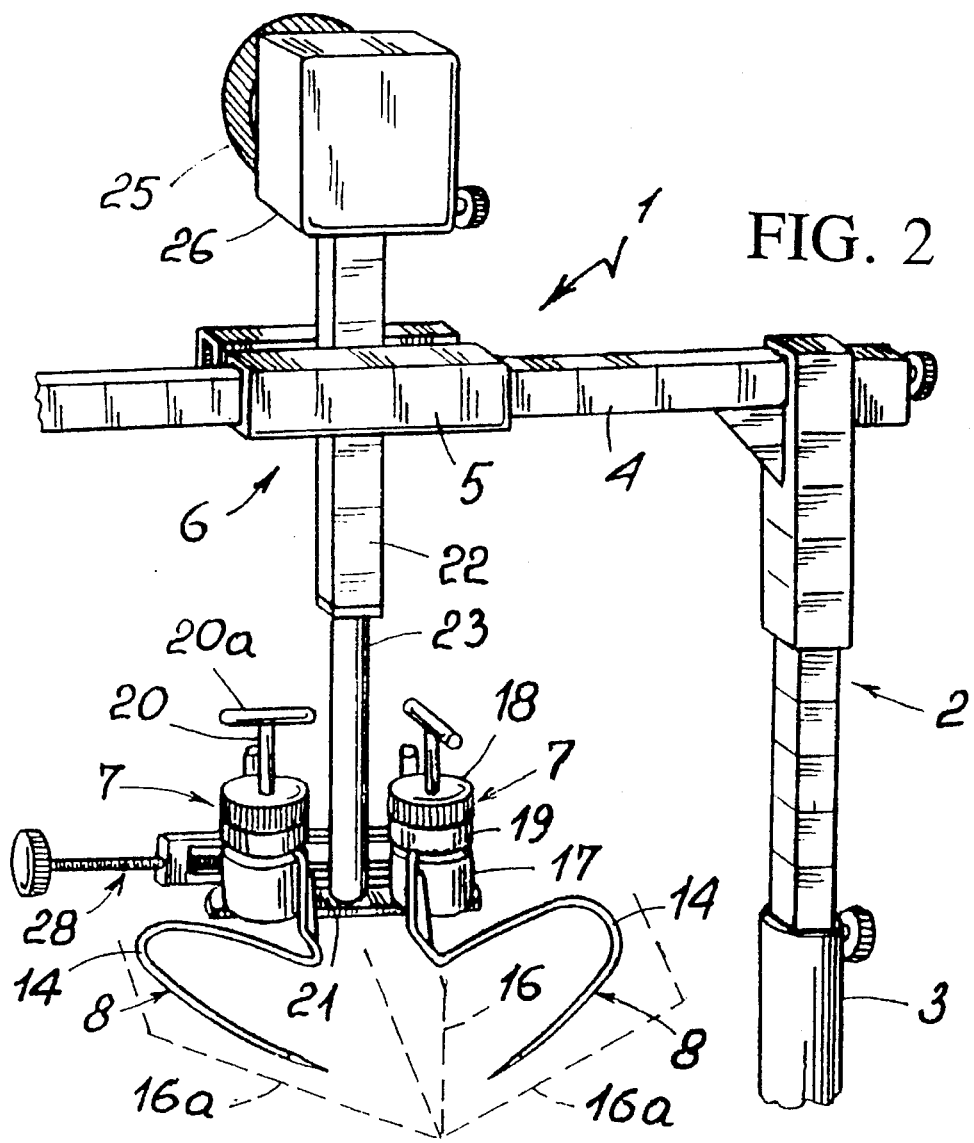
FIG. 2

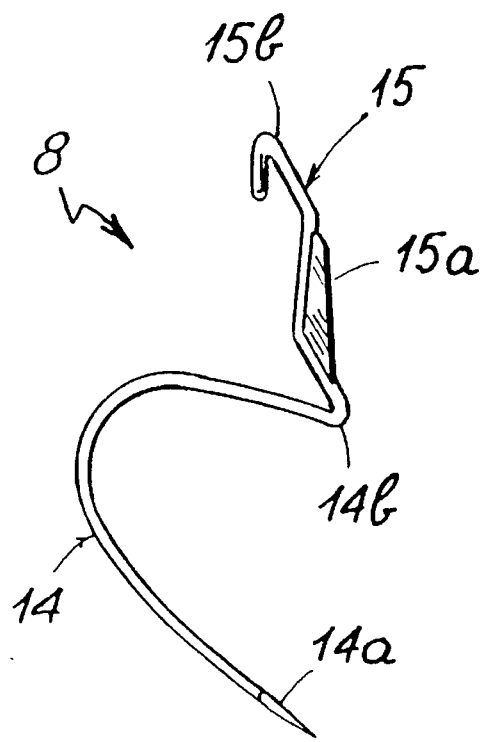
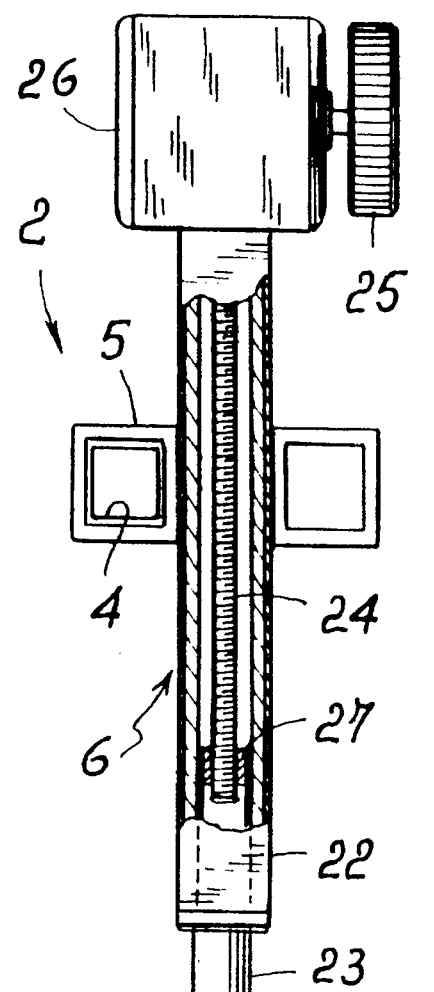
FIG. 4
FIG. 5

ELEVATOR DEVICE FOR AN ABDOMINAL WALL, IN VIDEOLAPAROSCOPIC SURGICAL OPERATIONS

BACKGROUND OF THE INVENTION

The present invention relates to an elevator device for an abdominal wall, in videolaparoscopic surgical operations, of the type comprising mechanical elements for tensioning the abdominal wall, and movement means engaging said mechanical elements.

It is known that in the surgery field there is a mini-invasive operative method availing itself of the so-called "laparoscopy" or "videolaparoscopy", which enables operations in the abdominal cavity to be executed without causing serious traumas.

Presently, this type of surgery is for example used for extirpation of cholecyst, ovarian cysts, removal of inguinal hernia, operations of various types on colon, lever and bile-ducts, and peritoneum.

According to said operative method, the abdominal wall is provided to be raised so as to form an appropriate work chamber, into this chamber being then introduced through holes, both instruments enabling an endoscopic visualization of the peritoneal cavity and instruments enabling a surgical operation.

In order to form this chamber, the method of injecting carbon dioxide or another gas into the peritoneal cavity, to create the so-called "pneumoperitoneum" has been known for a long time. Peritoneum, as well-known, is a serous membrane enveloping the abdominal viscera and partly the pelvic cavity.

This method has many contraindications.

In fact, isolated accidents such as perforation of the intraabdominal viscera and relevant blood vessels are possible; there are inconveniences connected with dissolution of carbon dioxide in the human organism, such as for example modification of the blood pH which gives rise to acidosis, and release of catecholamines is possible, which results in intra-operative hypertensive crises.

In addition, injection of gas makes it difficult to operate on patients suffering from cardiopathy, as they hardly tolerate an increase in the intraabdominal pressure, and increases post-operative pains, so that the patients' stay in hospital becomes longer.

Then other time-consuming operations may be necessary, such as previous washings of the peritoneal cavity and in addition, while the operation is taking place, fumes produced by the radio knife during the cutting and coagulation steps cannot be sucked, in order not to suck the carbon dioxide too therewith.

Also required is the use of particular and expensive cannulas, of the so-called "trocars" type provided with a dual valve, and also of special instruments, to avoid escape of the injected gas.

Attempts have been made to solve the above drawbacks by the use of raising methods no longer based on the injection of carbon dioxide or other gases into the abdominal cavity, but based on devices including mechanical tensioning elements that are inserted into the abdomen, and movement means capable of lifting these elements so as to form said work chamber for videolaparoscopic surgical operations.

The insertion of metal wires into the abdomen is for example known, said wires being maintained raised by chains, threads or handles vertically overlying each metal wire and penetrating the patient at both ends of each metal wire. Also known is the solution providing the introduction into the peritoneal cavity of two blades or bars pivoted on each other at one end. The two blades are kept close to each other when they are introduced into the peritoneal cavity through a single hole and are then compass-wise spaced apart from each other and then vertically raised.

Up to now these methods have not given satisfactory results. Actually, the above methods have avoided the "pneumoperitoneum", but have shown both the drawback of the so-called "tent effect" that greatly reduces the space at the surgeon's disposal, and the drawback of an important traumatism. Said "tent effect" consists in that the raised abdomen portion and the immediately surrounding portions tend to bend downwardly like the walls of a tent, thereby reducing visibility and the available operative space.

As regards traumatism, it is caused by the great invasive action of the mechanical tensioning elements introduced into the peritoneal cavity.

In fact, stresses transmitted to the abdominal tissues are not distributed and at some areas stress concentrations occur which can give rise to traumas to the tissues.

Practically, in order to avoid these traumas it is necessary to renounce all attempts of achieving a wide elevation of the abdominal wall.

It should be also noted that raising of the abdominal wall needs great efforts that give rise to big local deformations in the mechanical tensioning elements which cannot be bulky. These deformations may bring about further risks of traumas or local tissue injuries and in addition reduce the width of the work chamber.

SUMMARY OF THE INVENTION

Under this situation, the technical task underlying the present invention is to provide a device capable of substantially eliminating the above drawbacks.

Within the scope of this technical task it is an aim of the invention to provide a device featuring a minimum invasive action and capable of reducing post-operative pain and the duration of the patients' stay in hospital, while at the same time enabling a greater and improved elevation of the abdominal wall.

Another aim of the invention is to provide a device having features of maximum functionality and minimum invasive action under stress as well.

The technical task mentioned and the aim specified are substantially achieved by an elevator device for an abdominal wall, in videolaparoscopic surgical operations, as claimed in the following claim 1.

BRIEF DESCRIPTION OF THE DRAWINGS

The description of the elevator device according to the invention is now given by way of non-limiting example, with reference to the accompanying drawings, in which:

FIG. 1a diagrammatically shows raising of an abdominal wall by an elevator device according to the invention;

FIG. 1b diagrammatically shows a subsequent tensioning of said abdominal wall;

FIG. 2 is a perspective view of the device of the invention;

FIG. 4 shows a needle of the device in a first embodiment thereof;

FIG. 5 is a side view of one device portion;

DESCRIPTION OF THE INVENTION

Figure 3:
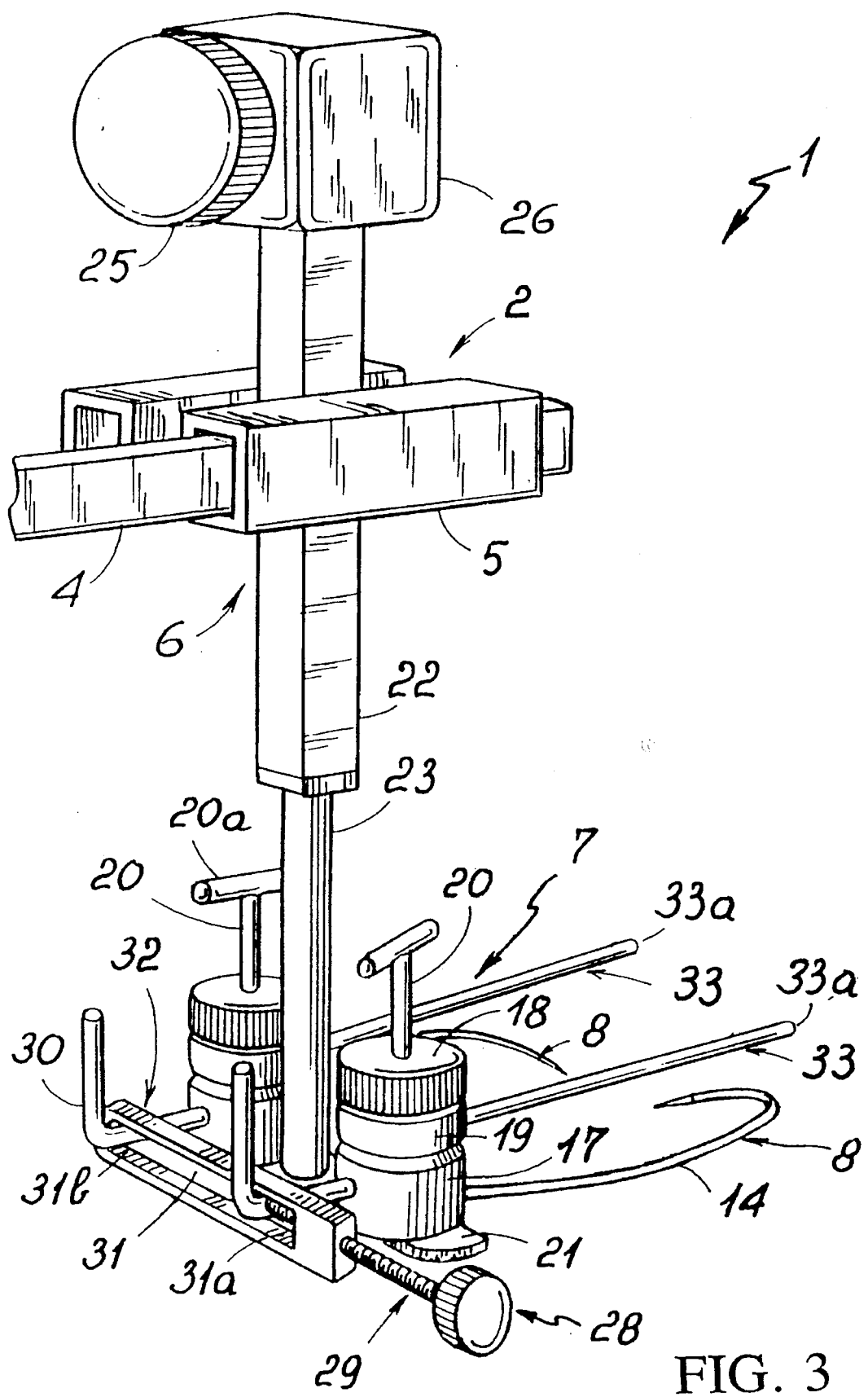
FIG. 3 is another perspective view of the device to an enlarged scale with respect to the preceding figure.
Figure 6:
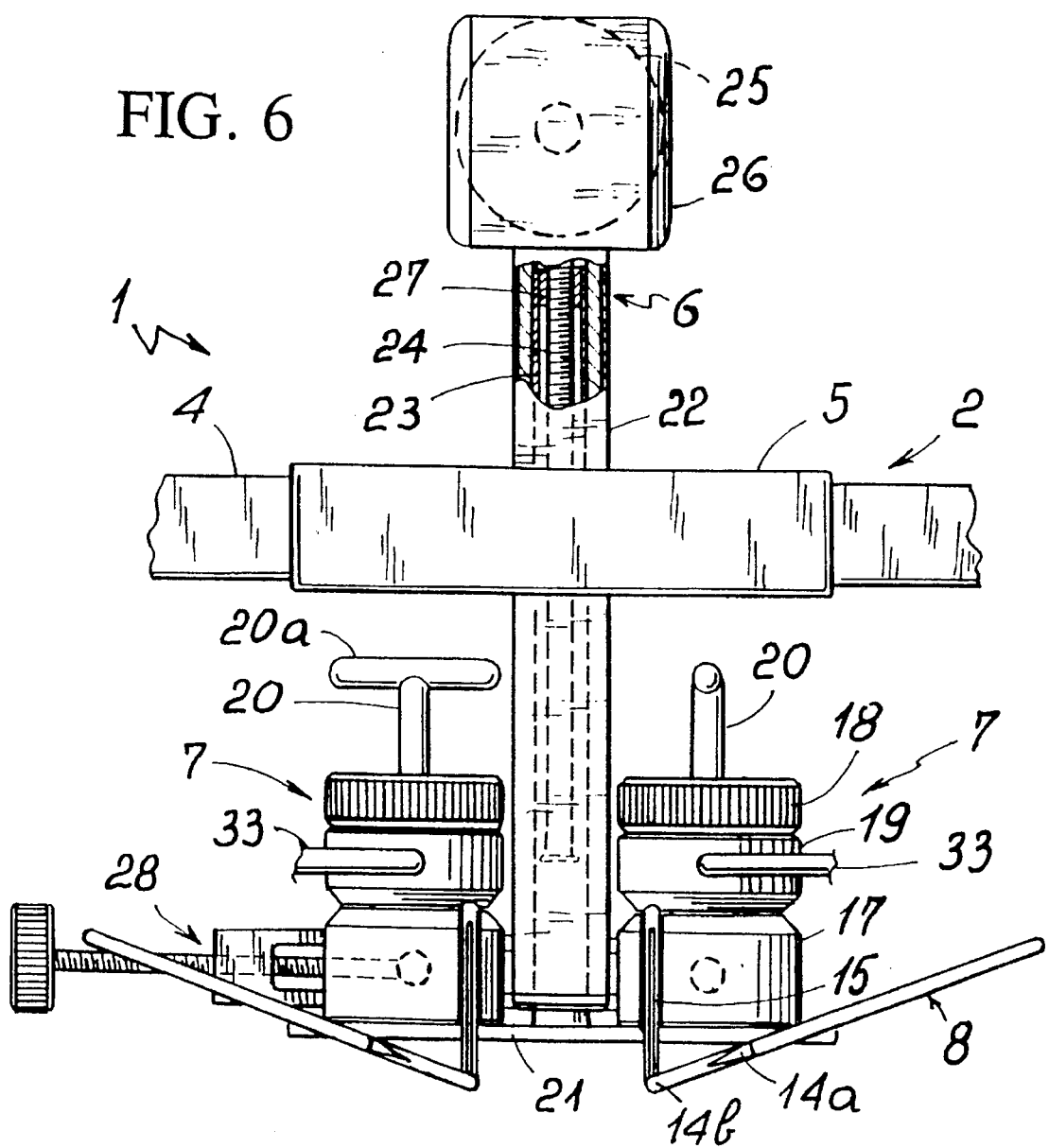
FIG. 6 is a front view of the device shown in FIG. 5.
Figure 7:
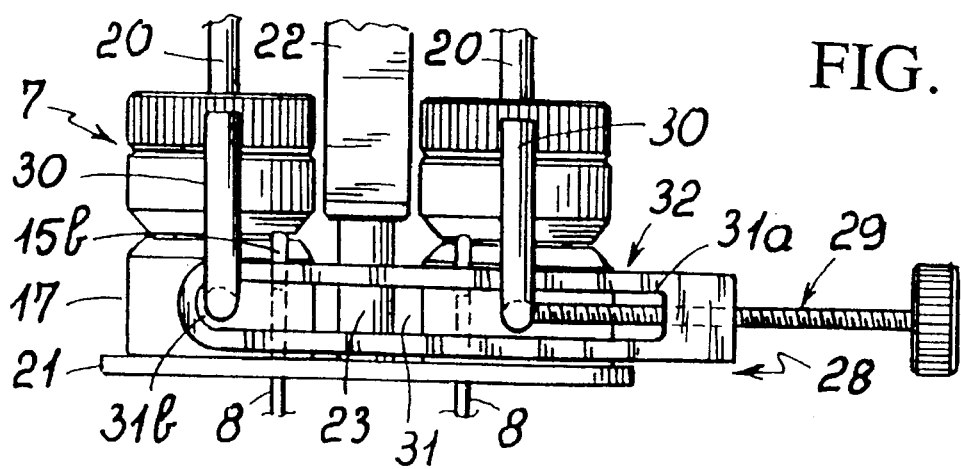
FIG. 7 is an elevational rear view of the device portion close to the needles.

Referring to the drawings, the device according to the invention has been generally identified by reference numeral 1.

It comprises movement means 2 having a post 3 to be fastened to the operative table, a cross-piece 4 lockable at an adjustable height to the post 3, a slider slidably mounted on the cross-piece 4, and raising members in engagement with the slider 5.

In the figures, the slider 5 is formed of two tubes disposed side by side, to be selectively engaged to the cross-piece 4. Connected to the raising members 6 are two clamping units 7 supporting mechanical tensioning elements embodied by shaped needles 8.

The shaped needles 8 are adapted to be partly introduced into the subcutaneous tissue 9 of an abdominal wall 10.

As known, an abdominal wall comprises a surface skin 11 and an underneath layer of subcutaneous tissue 9 followed by a muscle layer 12 and the peritoneum 13.

The shaped needles are preferably made of special biocompatible stainless steel.

Each shaped needle 8 comprises a plunging portion 14 to be buried into the subcutaneous tissue, in the form of an arc, and a hooking portion 15 adapted to be fastened to one clamping unit 7.

More particularly, each plunging portion 14 with a diameter of about 4 mm for example, is provided with a free end 14a which is sharpened and with an attachment end 14b opposite the sharpened end 14a.

When in engagement with a respective clamping unit 7, the concavities of the plunging portions 14 face each other, i.e. they substantially define an open ring in plan.

Due to the conformation of the shaped needles 8 shown in FIGS. 1 to 7, in the absence of stresses, each plunging portion 14 is disposed in a lying plane 16a oblique to a vertical plane 16 disposed intermediate between the shaped needles 8.

The lying planes 16a of the two plunging portions 14 intersect with each other forming an upwardly concave angle. The sharpened ends 14a are always turned downwardly and in addition they are at a higher level than the attachment ends 14b, as visible in FIGS. 5 and 6.

Each hooking portion 15 has a stiffening region 15a formed of a gusset plate or a rib and disposed close to the attachment end 14b.

In this manner, the torsional and bending stresses acting on the shaped needles 8 are exactly concentrated at the attachment ends 14b and consequently localized regions are created (which are not inside the patient) which are more critical in terms of fractures to which the plunging portions 14 may be subjected.

In addition, each hooking portion 15 has a hook 15b to be coupled with the related clamping unit 7.

Each clamping unit 7 receives a hook 15b which is fitted thereinto through a basic engaging body 17, an upper clamping element 18 provided with an operating knurling and an intermediate locking plug 19.

The clamping element 18 is threadingly mounted on the engaging body 17 and the latter is provided with cuts so that the hook 15b may be tightly fitted thereinto.

The locking plug 19, made of sterilisable plastic material for example, constitutes a means against accidental untightening of the screw coupling between the two components 17 and 18, between which it is inserted, and prevents rubbing of metal parts during tightening from generating particulates which are dangerous for the operative field.

The clamping units 7 are connected to the raising members 6 by pivot pins 20 vertically emerging from a base plate 21 and defining vertical rotation and sliding axes for the shaped needles 8 and the clamping units 7 themselves.

Pivots 20 in fact are of a height sufficient to enable lifting and sliding along them of the clamping units 7 or the individual elements of said units during the mounting step.

Each pivot 20 is delimited at its upper part by a transverse bar 20a adapted to prevent the clamping units 7 from slipping off when they slide along the pivots 20, when a patient is being moved for example.

The raising members 6 terminate at said base plate 21 by a pair of telescopic tubes sliding one within the other and comprising an outer tube 22 and an inner tube 23.

The outer tube 22 is integral with slider 5 and is passed through by an operating screw 24 (FIG. 5) rotatable either by means of a motor or manually, through a knob 25 and intermediate gear wheels held in a box-shaped body 26.

The knob 25 and box-shaped body 26 can be positioned and turned in such a manner as to facilitate interventions by the person who operates the device.

Rotatably coupled with the operating screw 24 is a nut screw 27 integral, at its upper end, with the inner tube 23. Said inner tube is connected at its lower part with the base 21. The above described raising members 6 enable the surgeon not to exert on the knob 25 an excessive torque capable of altering the surgeon's muscular condition giving rise to an inappropriate trembling of his hands and a reduction in his tactile reactions.

The movement means 2 comprises spacing members 28 designed to move the shaped needles 8 away from each other.

Said spacing members 28 are adapted to impart opposing rotations to the clamping units 7 about the pivots 20, that is about the vertical rotation axes defined by said pivots.

In greater detail, as shown in FIG. 3, each engaging body 17 is integral with a tailpiece 30 projecting from the body 17, on the side opposite to the shaped needles 8.

Tailpieces 30 are slidably housed in a slot shaped opening 31 of an element 32 in which a lead screw 29 is inserted. The lead screw 29 is rotatably fitted in the element 32 at one end 31a of the opening 31, so as to have a translation direction parallel to the opening 31 and at the inside of same.

The lead screw 29 abuts against the first tailpiece 30, whereas the element 32 abuts against the second tailpiece 30 at a second end 31b of the slot shaped opening 31.

Finally, bar-shaped external support elements 33 are provided to advantage; they develop above the needles starting from the clamping units 7 and are adapted to define auxiliary anchoring means for the shaped needles 8 and other equipments used in surgical operations, and generally intraperitoneal means.

The support elements 33, drawn in the form of a straight line in FIG. 3, may have any appropriate shape and their ends 33a are disposed in cantilevered fashion substantially above the sharpened needle ends 14a and close thereto.

Advantageously, the support elements 33 can be of the telescopic type so that the length of same can be adjusted depending on requirements, and/or of the articulated type, so that their position too can be adjusted.

Figure 8:
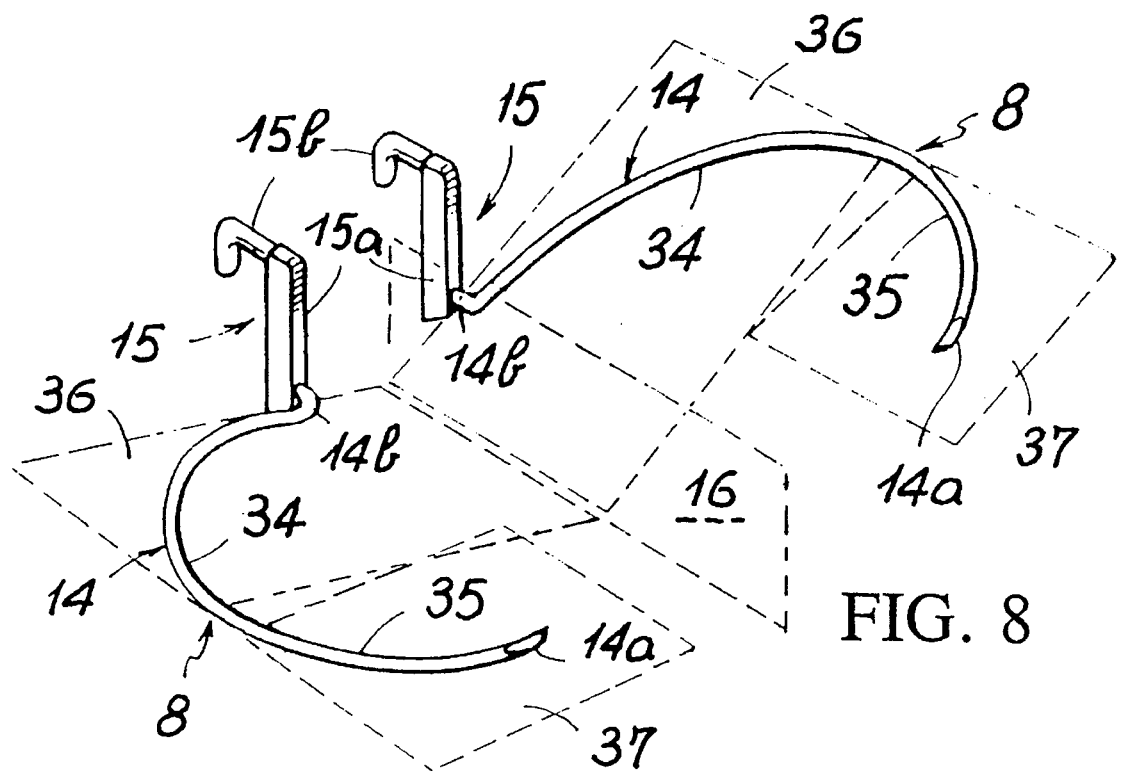
FIG. 8 is a perspective view of the device needles, in a second embodiment.

A second embodiment of the shaped needles 8 is shown in FIG. 8; they still have plunging portions 14 with cavities turned towards the vertical plane 16 disposed intermediate between the needles.

Actually, the shaped needles 8 as shown in FIG. 8 are multiplanar needles, i.e. they have plunging portions 14 comprising an initial length 34 starting at the attachment end 14b, and an end length 35 terminating at the sharpened end 14a, which are disposed in different planes.

In fact, when they are in engagement with the clamping units 7 and in the absence of stresses, the initial lengths 34 diverge from each other, rise ramp-wise relative to a horizontal base plane passing through the attachment ends 14b and are substantially placed in first lying planes 36 oblique to and symmetrical with the vertical plane 16.

The first lying planes 36 converge so as to form an upward concave angle. Practically, they are disposed so as to have points of increasing height with the increase of their distance from the vertical plane 16.

The end lengths 35, on the contrary, converge from each other and descend with a slight inclination, so that their sharpened ends 14a are located at raised positions with respect to the attachment ends 14b, and are disposed in second lying planes 37 which are symmetrical with each other as well with respect to the vertical plane 16, but the obliquity of which is less than that of the first lying planes 36.

Figure 9:
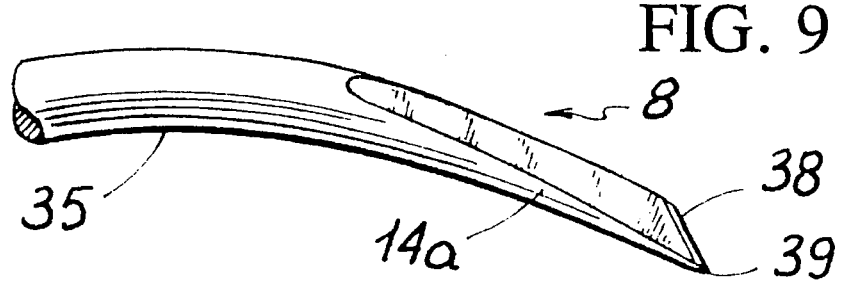
FIG. 9 is a perspective view of the end of a needle shown in FIG. 8.

In the embodiment shown in FIG. 8 the hooking portions 15 have a stiffening region 15a made of a stiff plate. In the multiplanar shaped needles 8, the sharpened ends 14a (FIGS. 9 and 10) are provided with tapers making them flat and causing them to terminate with front cutting edges 38, like knives, disposed in the respective second lying planes 37.

In addition, each front cutting edge 38 forms a lateral point 39 on one side and an angle greater than 90 degrees on the other side. The lateral point 39 is located on the side of each front cutting edge 38 facing the other needle and the intermediate vertical plane 16.

Figure 10:
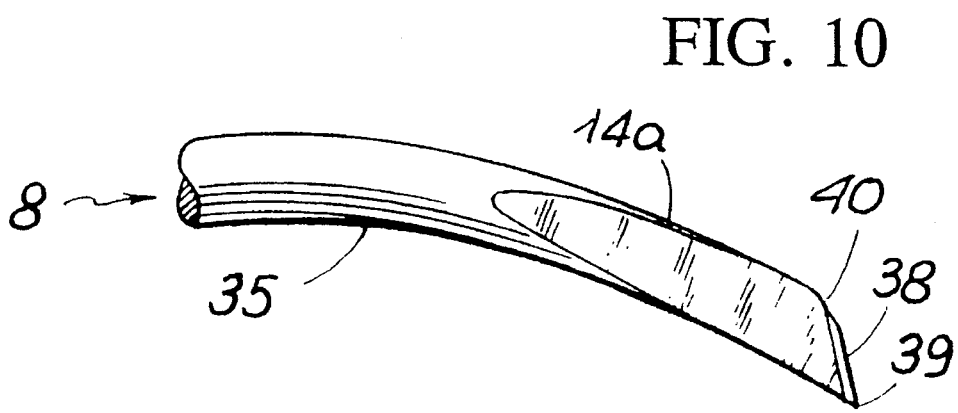
FIG. 10 is a plan view of the needle end shown in FIG. 9.

Furthermore, as shown in FIG. 10, on the opposite side from the lateral point 39, at said angle greater than 90 degrees, the front cutting edge 38 is eliminated by means of a chamfer 40.

Operation of the device is as follows.

A surgeon first introduces the shaped needles 8 into the subcutaneous tissue 9, preferably when said needles are not yet in engagement with the clamping units 7.

Locking of the shaped needles is carried out by raising the locking plugs 19 and the clamping elements 18, fitting the hooks 15b into the engaging bodies 17 and then restoring the elements 18 and 19 to the proper place.

The clamping units 7, once formed, can freely slide together with the shaped needles 8, along the pivot pins 20. In this manner, the patient and the device do not form a rigid assembly.

Once these operations have been completed, the knob 25 of the raising members 6 is acted upon and elevation of the abdominal wall 10 is carried out (FIG. 1a). Then, through the lead screw 29 of the spacing members 28 a rotation of the needles 8 about the vertical axes of pivots 20 is executed (FIG. 1b). In fact, the tailpieces 30 are moved close to each other by the combined action of the thrust ends of the lead screw 29 and element 32.

As a result, tensioning in a direction transverse to the raising direction is imparted to the tissues included between the two shaped needles.

It is therefore possible to exploit the elasticity of this portion of the abdominal wall and reduce the tissue stresses on the sides of the tissues included between the needles, already tensioned during the elevation step.

The step involving spacing apart of the needles therefore enables the stress condition in the tissues to be made even, thereby avoiding big concentrations of forces that would tend to traumatize said tissues and could also give rise to separation of the muscle fascia 12 from the subcutaneous tissue 9, which would inhibit a correct raising of the peritoneum 13 and thus the formation of an optimal work chamber.

It is pointed out that mutual moving apart of the needles nullifies the "tent effect", i.e. bending downwardly of the tissues included between the two shaped needles, as well apparent from a comparison of FIGS. 1a and 1b.

The reduction of stresses in the tissues disposed laterally of those included between the needles may also allow a further reduced raising of the shaped needles.

From a mechanical point of view, the mutual spacing apart of the needles enables the torque acting on the needles and due to the vertical load to be reduced, because there is a tendency to the generation of a stress condition which will result in a horizontal force applied to the center of each needle.

The needles have their sharpened end 14a facing downwardly, so that they do not damage the tissues during the raising step, which sharpened end is however more raised than the attachment end 14b, in order to compensate for the downward bending.

The shaped needles 8 have a tendency to bend centrally and at the end, but in particular the shape of the multiplanar needles 8 shown in FIG. 8 prevents the end lengths 35 from bending under stress to such an extent that they can no longer maintain the desired operative volume. In fact the end lengths 35 have a well-raised starting position and can bend without serious inconveniences.

The sharpened ends 14a of the multiplanar shaped needles 8 are upwardly flat and therefore, in addition to not causing cuts during the raising step, also due to the fact that they are turned downwardly, they also cooperate in carrying out raising.

During the widening step said sharpened ends 14a move away from each other still without making any cuts, due to their shape that has no point turned outwardly.

In addition, the multiplanar shaped needles 8 enable a greatly facilitated fitting: the lateral point 39 and the inclination of the front cutting edge 38, as well as chamfer 40 establish a preferential penetration direction tending to gradually bend towards the vertical symmetry plane 16, in accordance with the needle shape.

The external support elements 33 can be used for fixedly anchoring the endoscope or surgical equipments such as cannulas or trocars.

In this manner both an optimal positioning of the intraperitoneal means and a smaller traumatism are achieved, the former because in this case the positioning of said means varies automatically with the elevation of the abdominal wall, the latter because the mechanical stresses transmitted to the instruments are not discharged any longer on the patient's tissue.

If elements 33 are of the telescopic or articulated type, they can always furnish an optimal support as regards position, and can also be adjusted each time.

The invention achieves important advantages.

The subcutaneous tissue is the only tissue with which the device directly interacts.

In addition, the sharpened ends after the lacerations they produce during the introduction step, do not cause other lacerations when the needles are moved by the movement means 2: due to the conformation of the shaped needles and their sharpened ends, during the elevation and spacing steps the sharpened ends cannot slide backwards into the lacerations already formed in the subcutaneous tissue.

It should be also recognized that the device according to the invention gives rise to an even tensioning of the tissues and exploits all elasticity characteristics of same.

By virtue of this evenness in tensioning and the wide distribution of said tensioning, the invasive action is minimum.

In addition, a greater elevation of the abdominal wall is allowed, due to the fact that the absence of localized overstresses enables the muscular layer and the peritoneum to be raised without any danger of separation of same from the subcutaneous tissue.

The absence of overstresses is also promoted by the vertical oscillating movement of the shaped needles that do not rigidly engage a patient.

I claim:

1. An elevator device for an abdominal wall, in videolaparoscopic surgical operations, comprising mechanical elements for tensioning an abdominal wall (10) and movement means (2) for said mechanical tensioning elements, wherein said mechanical tensioning elements are shaped needles (8) having sharpened ends (14a) and being adapted to be introduced into a subcutaneous tissue (9) of said abdominal wall (10), and wherein said movement means (2) comprises raising members (6) for said shaped needles (8) and spacing members (28) designed to move said shaped needles (8) away from each other, said raising members (6) and spacing members (28) being adapted to carry out raising of said abdominal wall (10) and tensioning of the same wall transversally of said raising.

2. The device as claimed in claim 1, wherein said mechanical tensioning elements consist of two shaped needles (8) having respective sharpened ends (14a) and defining two plunging portions (14) substantially in the form of an arc, said plunging portions (14) having mutually facing concavities.

3. The device as claimed in claim 2, wherein said shaped needles (8) have said plunging portions (14) disposed substantially along lying planes (16a) oblique to a vertical plane (16) intermediate between said shaped needles (8), said lying planes (16a) forming an upwardly concave angle.

4. The device as claimed in claim 2, wherein said plunging portions (14) comprise initial lengths (34) and end lengths (35) provided with said sharpened ends (14a), wherein said initial lengths (34) diverge from each other and extend in first lying planes (36) oblique to a vertical plane (16) intermediate between said shaped needles (8), and wherein said end lengths (35) are mutually convergent and extend in second lying planes (37) having a lower inclination than said first lying planes (36) with respect to said vertical plane (16), said first and second lying planes (36, 37) forming upwardly concave angles.

5. The device as claimed in claim 2, wherein said plunging portions (14) are shaped in a manner causing said sharpened ends (14a) to directed downwardly.

6. The device as claimed in claim 2, wherein said sharpened ends (14a) have front cutting edges (38) which are flattened and extend in the lying planes of said plunging portions (14).

7. The device as claimed in claim 6, wherein said front cutting edges (38) are shaped in a manner defining respective lateral points (39), said lateral points (39) facing each other.

8. The device as claimed in claim 7, wherein said front cutting edges (38) are chamfered opposite said lateral points (39).

9. The device as claimed in claim 2, wherein each of said shaped needles (8) has a respective attachment end (14b) of said plunging portions (14), said attachment end is adapted to define a localized fracture area; and said attachment end is located adjacent a stiffening region (15a).

10. The device as claimed in claim 1, wherein said shaped needles (8) are in engagement with said movement means (2) at two pivots (20) spaced apart from each other and defining substantially vertical rotation axes for said shaped needles (8).

11. The device as claimed in claim 10, wherein said shaped needles (8) are capable of movement in a substantially vertical direction along said pivots (20).

12. The device as claimed in claim 10, wherein said spacing members (28) for said shaped needles (8) are adapted to impose rotations to said shaped needles (8) about said rotation axes.

13. The device as claimed in claim 10, wherein said raising members (6) for said shaped needles (8) engage said pivots (20) at the ends of said pivots 20.

14. The device as claimed in claim 1, further comprising external support elements (33) which are in engagement with said movement means (2) and are embodied by bars extending above said shaped needles (8).

* * * * *